(12) United States Patent
Urrutia

(10) Patent No.: US 6,183,447 B1
(45) Date of Patent: *Feb. 6, 2001

(54) MEDICAL DYE DELIVERY SYSTEM

(76) Inventor: Hector Urrutia, 2404 W. Augusta Sq., McAllen, TX (US) 78503

( * ) Notice: Under 35 U.S.C. 154(b), the term of this patent shall be extended for 0 days.

This patent is subject to a terminal disclaimer.

(21) Appl. No.: 09/316,090

(22) Filed: May 21, 1999

Related U.S. Application Data

(63) Continuation-in-part of application No. 08/954,661, filed on Oct. 20, 1997, now Pat. No. 6,017,332.

(51) Int. Cl.[7] .................................................. A61M 5/00
(52) U.S. Cl. ................................................ 604/247
(58) Field of Search ....................... 604/246, 254, 604/247, 30, 31, 256; 137/403, 192, 399, 451, 433

(56) References Cited

U.S. PATENT DOCUMENTS

| | | |
|---|---|---|
| 1,144,657 | 6/1915 | Keller . |
| 1,788,058 | 1/1931 | Goerg . |
| 1,788,358 | 1/1931 | Goerg . |
| 2,214,290 | 9/1940 | Ward . |
| 2,294,237 | 2/1960 | Ellis . |
| 2,924,237 | 2/1960 | Ellis . |
| 3,227,173 | 1/1966 | Bertstein . |
| 3,790,306 | 2/1974 | Uefuji . |
| 4,208,881 | 6/1980 | Brademeyer et al. . |
| 4,323,173 | 4/1982 | Shannon . |
| 4,606,365 * | 8/1986 | Siposs ................................ 137/433 |
| 4,633,681 | 1/1987 | Webber . |
| 4,950,254 | 8/1990 | Andersen et al. . |
| 5,213,586 | 5/1993 | Welker . |
| 5,322,099 | 6/1994 | Langlois . |
| 5,373,957 | 12/1994 | Gryc . |
| 5,722,961 | 3/1998 | Fin . |
| 5,826,621 * | 10/1998 | Jemmott ............................. 137/853 |
| 6,017,332 * | 1/2000 | Urrutia ............................... 604/254 |

FOREIGN PATENT DOCUMENTS 1138647   6/1957   (FR) .

* cited by examiner

Primary Examiner—Sharon Kennedy
Assistant Examiner—Ann Y. Lam
(74) Attorney, Agent, or Firm—Oliff & Berridge, PLC

(57) ABSTRACT

A medical dye delivery system includes a medical dye container and a syringe for withdrawing the medical dye from the container and delivering the dye to a patient. A valve is disposed in the system having an inlet in flow communication with the medical dye container and an outlet in flow communication with the syringe. The valve includes a housing defining a flotation chamber with a valve seat and a flotation member disposed therein. The flotation member seals off the valve seat opening upon medical dye depletion, forcing any remaining fluid flow through a bypass channel that provides restricted flow to provide a tactile warning to the operator of the system that the medical dye container is depleted, yet allow the operator to purge remaining dye from the system. In a preferred embodiment, the flotation member has first and second portions, with a density of the second portion being greater than a density of the first portion. The density of the second portion is sufficient to close against the valve seat, yet is still capable of being suspended above the valve seat when the flotation member floats in the volume of medical dye.

18 Claims, 10 Drawing Sheets

MEDICAL DYE DELIVERY SYSTEM

CROSS REFERENCE TO RELATED APPLICATION

This application is a continuation-in-part of U.S. application Ser. No. 08/954,661, filed Oct. 20, 1997, now U.S. Pat. No. 6,017,332.

BACKGROUND OF THE INVENTION

1. Field of Invention

This invention generally relates to a medical dye delivery system. More particularly, this invention relates to a system for delivering medical dye to a patient that minimizes the risk of introducing air into the dye delivery system. In a preferred embodiment, the invention relates to a medical dye delivery system that can be incorporated into a container for the dye, or can be a separate attachment.

2. Description of Related Art

Medical dye delivery systems are used by medical personnel to inject dye into a patient. The dye serves as a contrast medium for various diagnostic procedures, such as angiography. A medical dye delivery system generally includes a medical dye container that is connected in flow communication through a series of conduits to a mechanism for introducing dye into the patient. The mechanism draws the dye from the container and then directs the dye through the system and into the patient.

When performing diagnostic tests on a patient using the medical dye delivery system, the operator generally focuses on a visual display of the patient on a monitor and not on the amount of dye in the dye delivery system. This can cause the operator to unknowingly deplete the dye container, thereby drawing air into the system. To purge this air requires a time consuming effort. If the air is not purged, it may enter the patient and cause an embolism or other harmful effects. Further, the entrance of air in the system often occurs at a critical time of the procedure when even minor delays can have undesirable consequences.

Typical angiography quire between 80 cc and 300 cc of medical dye. In addition, the me dye is typically sold in containers holding 50 cc, 100 cc, or 150 cc, with 100 cc bottles being the most common. Because two or more containers may be required for an angiography procedure, the operator must be quickly made aware of when one container has been depleted to quickly switch to another, full container.

SUMMARY OF THE INVENTION

Accordingly, the present invention is directed to a medical dye delivery system that substantially obviates one or more of the problems due to limitations and disadvantages of the related art.

To achieve these and other advantages and in accordance with the purpose of the invention, as embodied and broadly described, the invention includes a medical dye container and a device for withdrawing medical dye from the container and directing the medical dye through a system flow path into a patient. A valve is disposed in the system, having an inlet in flow communication with the medical dye container and an outlet in flow communication with the withdrawing device. The valve includes a housing defining a chamber adapted for containing a volume of medical dye, a valve seat located in the chamber in flow communication with the outlet, and a flotation member. The flotation member is adapted for floating in the medical dye located in the chamber and is seated against the valve seat when the chamber is free of medical dye, thereby covering the valve seat opening.

The valve may also include a bypass channel in flow communication with the withdrawing device that is configured to provide restricted flow relative to flow through the valve seat opening when the medical dye is depleted. The restricted flow operates as a tactile warning to the operator that the medical dye is depleted and allows the operator to purge the remaining dye from the system flow path.

The valve can be incorporated into the medical dye container, or can be a separate element in fluid communication with the medical dye container.

Additional features and advantages of the invention will be set forth in the description which follows, and in part will be apparent from the description, or may be learned by practice of the invention. The objectives and other advantages of the invention will be realized and attained by the apparatus particularly pointed out in the written description and claims hereof, as well as the appended drawings. It is to be understood that both the foregoing general description and the following detailed description are exemplary and explanatory and are intended to provide further explanation of the invention as claimed.

BRIEF DESCRIPTION OF THE DRAWINGS

The accompanying drawings, which are incorporated in and constitute a part of this specification, illustrate embodiments of the invention and, together with the description, serve to explain the objects, advantages and principles of the invention. In the drawings.

DETAILED DESCRIPTION OF PREFERRED EMBODIMENTS

Reference will now be made in detail to the present preferred embodiments of the invention, examples of which are illustrated in the accompanying drawings.

Figure 1:
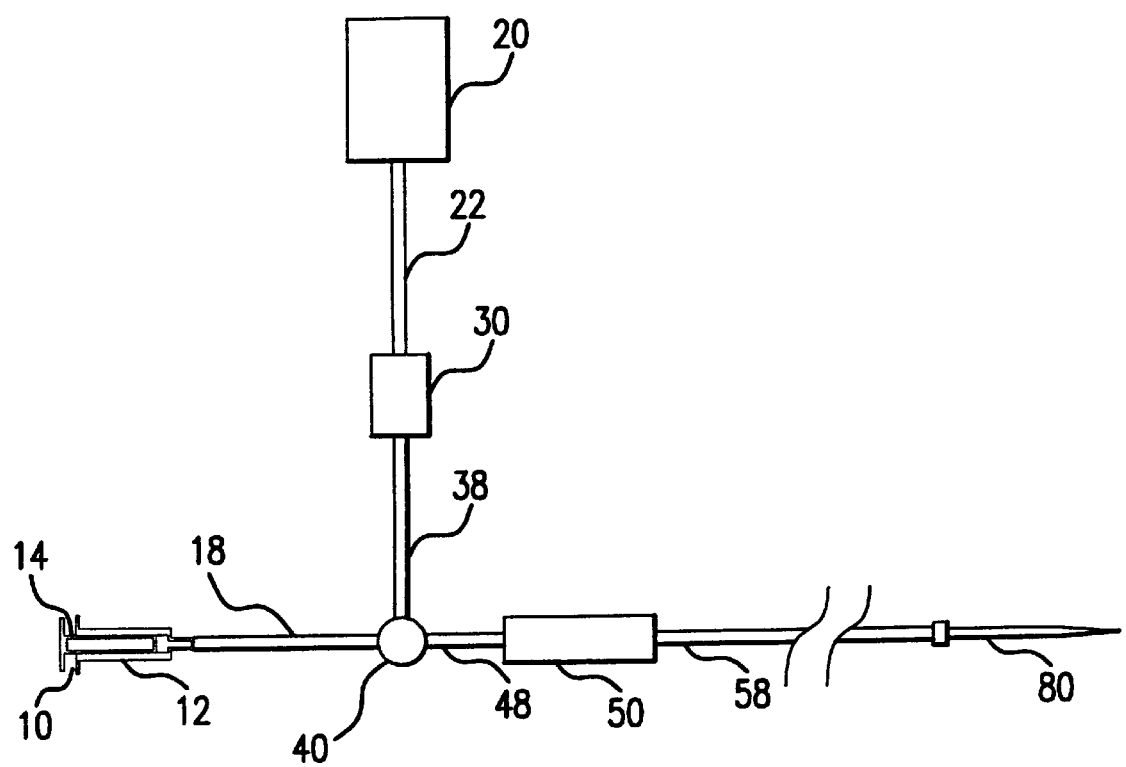
FIG. 1 is a diagram of a medical dye delivery system of the present invention.

A medical dye delivery system of the present invention is shown in FIG. 1. The system generally includes a medical dye container 20, a syringe 10 or other means for withdrawing medical dye from container 20 and directing the dye into the patient, a valve 30 for monitoring the level of medical dye in the system, a flow control valve 40 for regulating the flow of medical dye through the system, and a fluid delivery device 80 for channeling the medical dye into the patient. Optionally, a valve manifold 50 may be provided in the system to introduce alternative fluids into the patient prior to, during, or after the procedure. These components are connected in flow communication via a series of conduits to define a system flow path, as shown in FIG. 1, to deliver medical dye to the patient.

Medical dye container 20 may be a bag, bottle, or any other type of container that may be used for containing any of the medical dyes that are known in the art. The outlet of medical dye container 20 is connected through conduits 22 and 38 to a port of three-way flow control valve 40. A dye container air vent 24 (see FIG. 8) may be disposed near the outlet of container 20 to facilitate the flow of dye from container 20 and through the system.

A second port of flow control valve 40 is connected through a conduit 18 to syringe 10, and a third port of valve 40 is connected in flow communication with fluid delivery device 80 via conduits 48 and 58. Valve 40 selectively controls the flow of dye between container 20 and syringe 10 and between syringe 10 and delivery device 80, which may be any device for channeling medical dye into the patient, such as a needle, a cannula, or a catheter.

Control valve 40 may be a three-way valve having a valve element movable between at least two positions to direct flow. In the first position, the valve element operates to connect the first port of valve 40 in flow communication with the second port, but block flow through the third port. This position allows for medical dye to be drawn into syringe 10 from medical dye container 20, but prevents flow through delivery device 80. In the second position, the valve element connects the second port of valve 40 in flow communication with the third port, but blocks flow through the first port. This position allows for medical dye contained in syringe 10 to be injected into the patient via delivery device 80, but prevents back flow from syringe 10 to container 20.

Figure 2:
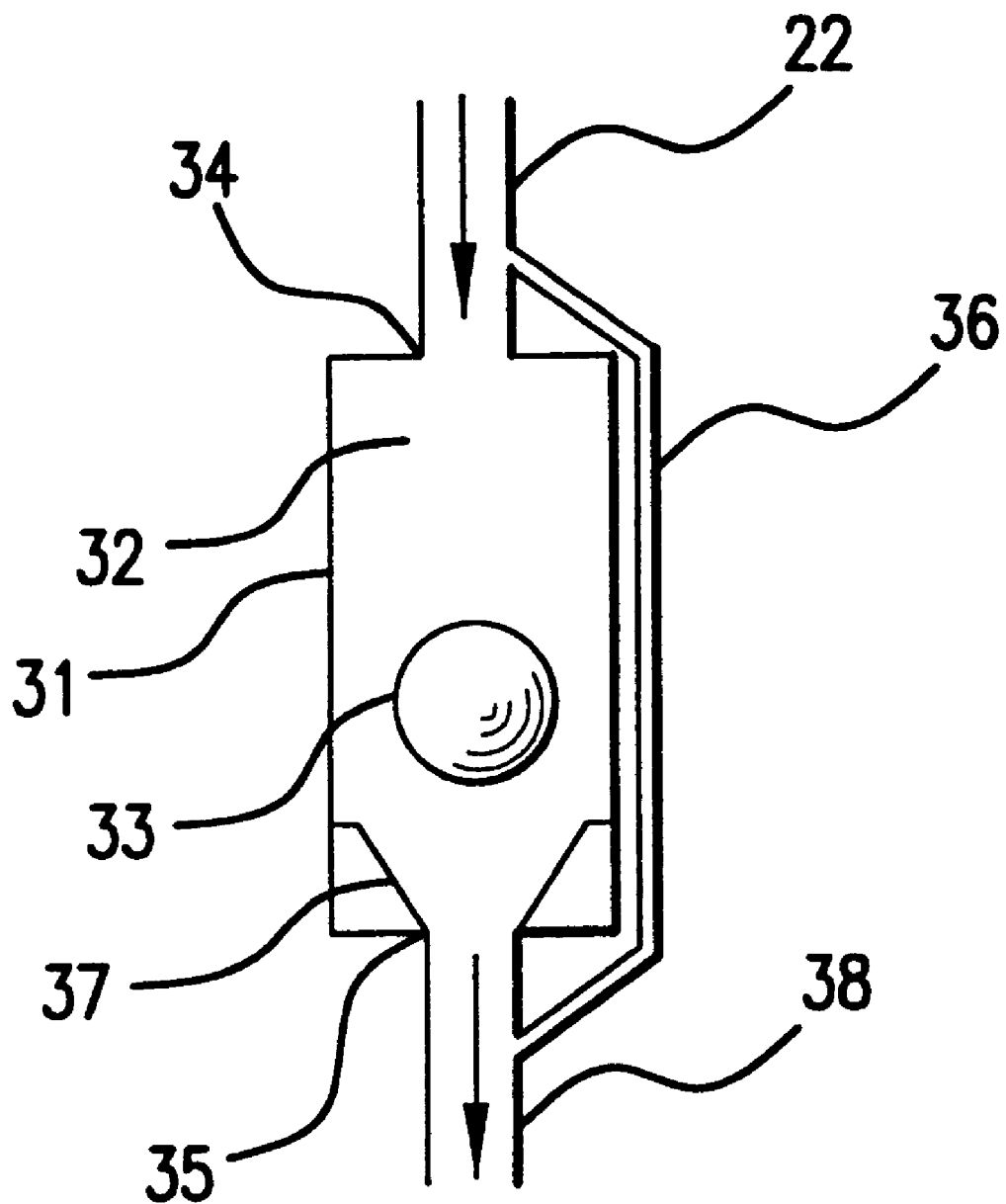
FIG. 2 is an elevation view of a valve for the medical dye delivery system shown in FIG. 1.

Valve 30 is disposed in the system flow path between container 20 and control valve 40 and is configured to alert the operator when medical dye container 20 is empty. As shown in FIG. 2, valve 30 includes a housing 31 enclosed at its top end by an inlet port 34 and at its bottom end by an outlet port 35. Inlet port 34 is connected through conduit 22 in flow communication with medical dye container 20 (FIG. 1). Outlet port 35 is connected through conduit 38 in flow communication with flow control valve 40 (FIG. 1).

Housing 31 also defines a flotation chamber 32, which acts as a reservoir for containing a volume of medical dye. A valve seat 37, having a substantially conical shape, is positioned in housing 31 and has an opening therethrough in flow communication with outlet port 35. A flotation member or ball 33, having a larger diameter than outlet port 35, is positioned in flotation chamber 32 and is adapted for floating in the volume of medical dye in flotation chamber 32. When flotation chamber 32 is empty of medical dye, flotation member 33 will seat on valve seat 37, thus blocking outlet port 35 and preventing the flow of air or other fluid therethrough.

To operate the medical dye delivery system, the operator sets control valve 40 so that container 20 is in flow communication with syringe 10. As shown in FIG. 1, syringe 10 includes a housing 12 and a plunger 14 that fits snugly within housing 12, forming a sliding fluid seal with the housing. When plunger 14 is withdrawn from housing 12, a vacuum is created, drawing medical dye through conduits 22, 38, and 18 and into syringe housing 12, and filling flotation chamber 32 with medical dye. Once syringe housing 12 contains medical dye, control valve 40 is set to connect syringe 10 in flow communication with delivery device 80, and prevent back flow between syringe and container 20. Syringe plunger 14 is then pushed into housing 12, forcing the medical dye through conduits 18, 48, and 58, and eventually into the patient via delivery device 80. These steps are repeated several times until sufficient dye is injected into the patient or the dye is depleted.

Prior to delivering dye to the patient, the system must be primed to expel air from the system flow path. However, since flotation chamber 32 of valve 30 is devoid of dye at this time, flotation member may seat against valve seat and block flow from container 20 to syringe 10. Thus, valve 30 must be manipulated so that flotation member 33 is not seated against valve seat 37 (e.g., valve is held in a horizontal orientation) while withdrawing plunger 14 from housing 12, thereby drawing the medical dye into valve 30. When sufficient medical dye enters flotation chamber 32, valve 30 can be returned to its normal vertical orientation.

When sufficient medical dye is in the system, flotation chamber 32 will contain sufficient medical dye to cause suspension of flotation member 33, thus allowing for unencumbered flow of medical dye through valve 30. However, when medical dye in medical dye container 20 is depleted, flotation chamber 32 will not contain sufficient medical dye to suspend flotation member 33. Flotation member 33 will then seat on valve seat 37, sealing the opening to outlet port 35 and preventing air from being drawn into the system through the dye container air vent by manipulation of syringe 10. Thus, valve 30 prevents the harmful effects associated with inadvertently injecting air into the patient.

When flotation member 33 becomes seated against valve seat 37, any dye remaining in conduits 38 and 18 cannot be drawn into syringe housing. However, the operator may desire to use this remaining medical dye to complete the procedure. To allow for the use of the remaining dye, valve 30 includes a bypass channel. When outlet port 35 is sealed by flotation member 33, air can be drawn through bypass channel, allowing the remaining fluid to be used. Bypass channel is configured to provide restricted flow through the system, thereby increasing the force necessary to draw fluid through the system with syringe 10. This gives the operator a tactile warning of the low volume of dye remaining in the system, but still allows the operator to use this remaining dye if so desired.

Various bypass channel configurations are shown in FIGS. 2–9. Unless otherwise noted, the previously-described components of valve 30 are identical for each of the embodiments.

Various other embodiments of the bypass channel, other than those disclosed, are contemplated so long as the bypass channel provides restricted flow through the system and provides a tactile warning of the low volume of dye remaining in the system.

In the embodiment shown in FIG. 2, bypass channel 36 has an inlet upstream of valve seat 37 and in flow communication with container 20 via conduit 22, and an outlet downstream of valve seat 37 and in flow communication with conduit 38. Thus, bypass channel 36 defines an alternate flow path between container 20 and control valve 40 that "bypasses" valve seat 37. While the bypass channel inlet shown in FIG. 2 is connected to conduit 22, it may also connect to housing 31 at any position above (i.e., upstream of) valve seat 37.

In this embodiment, the cross-section of bypass channel 36 is substantially smaller than the opening through valve seat 37, requiring the operator to use more force to draw the medical dye through bypass channel 36. "Substantially smaller," as used in this context, means small enough in comparison to the valve seat opening and port 35 to provide a noticeable difference in the force required to withdraw syringe plunger 14, thus providing a tactile warning to the operator that flotation member 33 is seated against valve seat 37. For example, the bypass channel diameter may be about 0.025–0.035 inches, while the valve seat opening is about 0.0625 inches or more.

Figure 3:
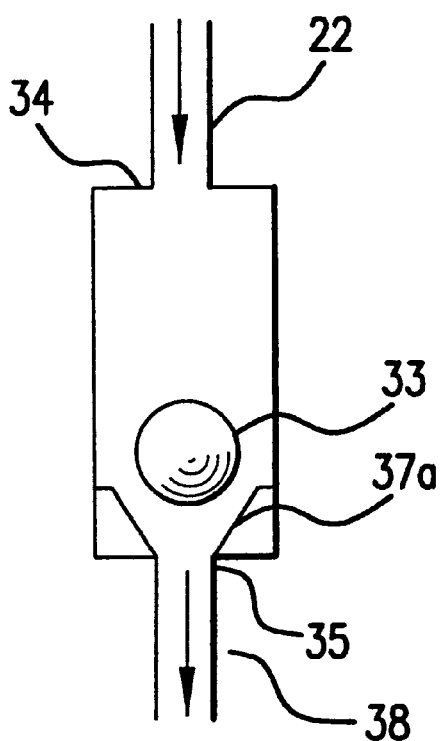
FIG. 3 is an elevation view of another embodiment of a valve for the medical dye delivery system shown in FIG. 1.
Figure 4:
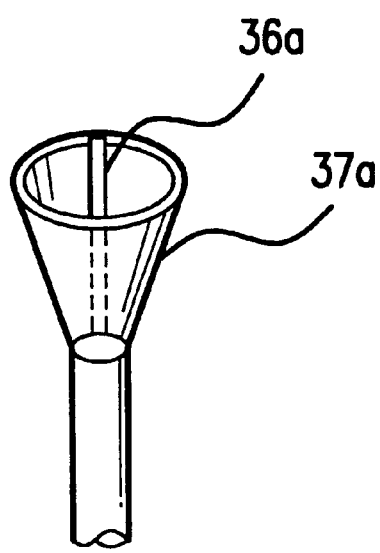
FIG. 4 is a perspective view of the valve shown in FIG. 3.

In another embodiment shown in FIGS. 3 and 4, bypass channel 36a is integrated into valve seat 37a, which is otherwise identical to valve seat 37 shown in FIG. 2. Thus, when medical dye container 20 is depleted, flotation member 33 will seat on valve seat 37a, but will not block slotted bypass channel 36a, thus permitting fluid to be drawn therethrough. Slotted bypass channel 36a has an opening substantially smaller than that of valve seat opening, and thus requires more force to draw the fluid through bypass channel 36a.

Figure 5:
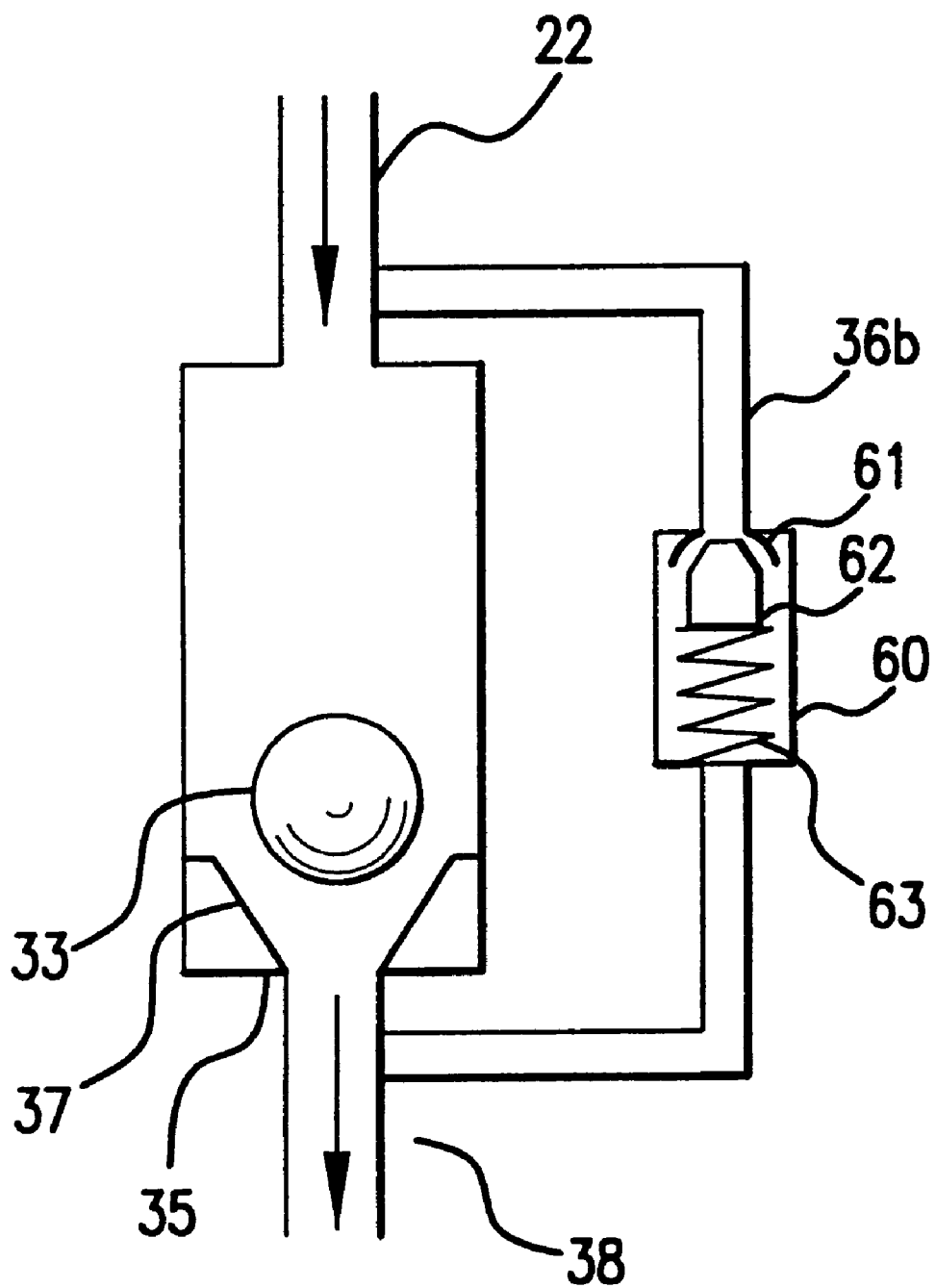
FIG. 5 is an elevation view of another embodiment of a valve for the medical dye delivery system shown in FIG. 1.

In another embodiment shown in FIG. 5, bypass channel 36b includes a bypass valve 60, including a valve seat 61 and a valve member 62 biased against valve seat 61 with a predetermined biasing force provided by a spring 63. When the opening through valve seat 37 is blocked by flotation member 33, the continued withdrawal by syringe 10 (FIG. 1) increases the suction force in the system. This increased suction force overcomes the predetermined biasing force provided by spring 63 and causes valve member 62 to become unseated form valve seat 61, thereby opening a fluid pathway through bypass channel 36b. The predetermined biasing force, which is preferably adjustable by the user, is selected so that it is sufficient to provide a tactile resistance that will alert the operator of the medical dye depletion, yet allow the operator to draw the remaining dye through the system. In this embodiment, the cross-section of the bypass channel is not critical since bypass valve 80 operates to provide the tactile resistance. However, a combination of a smaller bypass channel cross-section (relative to the valve seat opening diameter) and valve 80 may be used.

Figure 6:
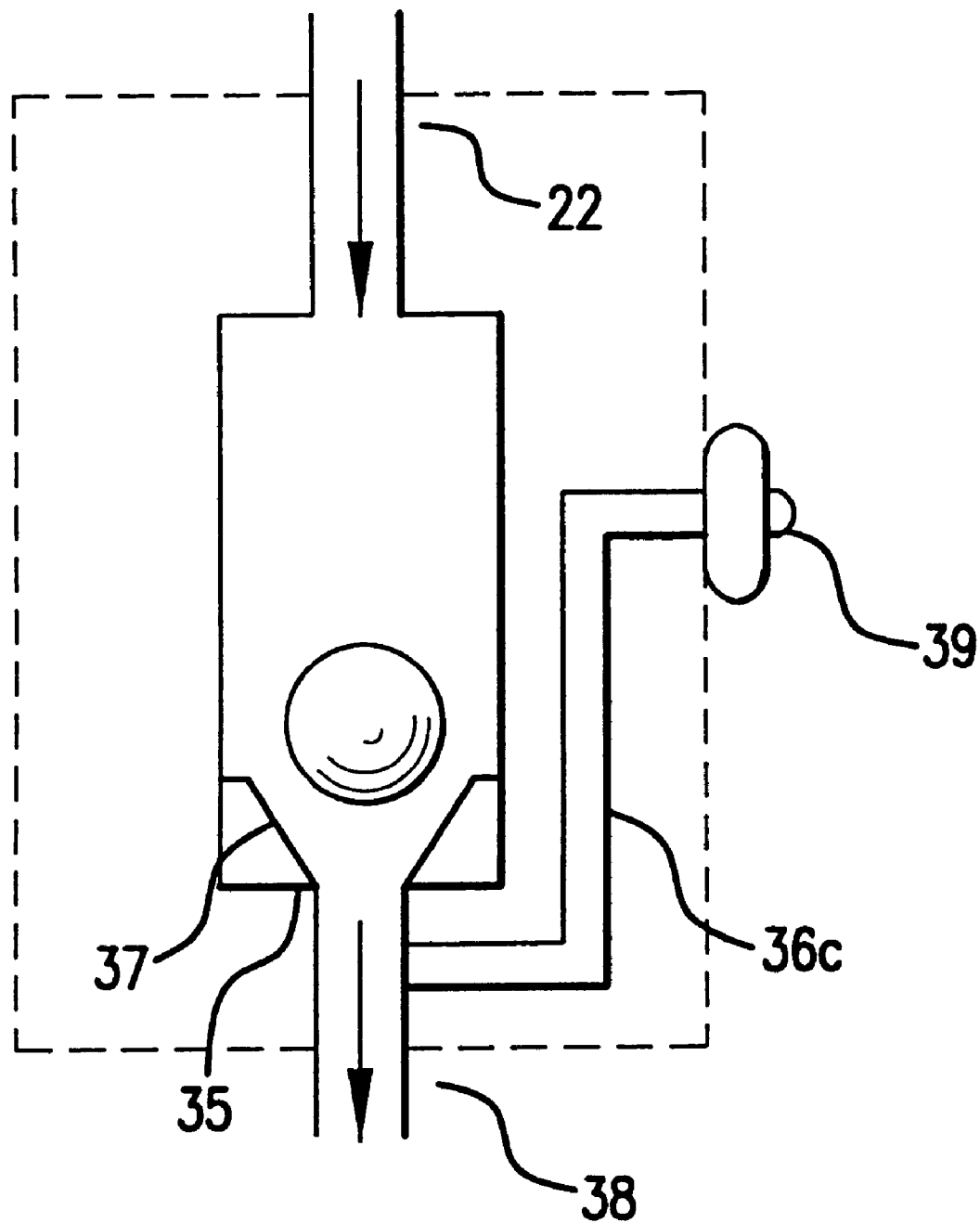
FIG. 6 is an elevation view of another embodiment of a valve for the medical dye delivery system shown in FIG. 1.

In another embodiment shown in FIG. 6, bypass channel 36c includes a first opening downstream of valve seat 37 and a second opening adjacent to an exterior wall of valve 30. A bypass valve 39 selectively allows external air to enter bypass channel 36c through the second opening. Bypass valve 39 may be a spring-biased valve similar to the one shown in FIG. 5, or may be a stopcock-like arrangement that the operator simply switches from a no-flow to a flow position when increased resistance, caused by the flotation member covering the valve seat opening, is detected.

Figure 7:
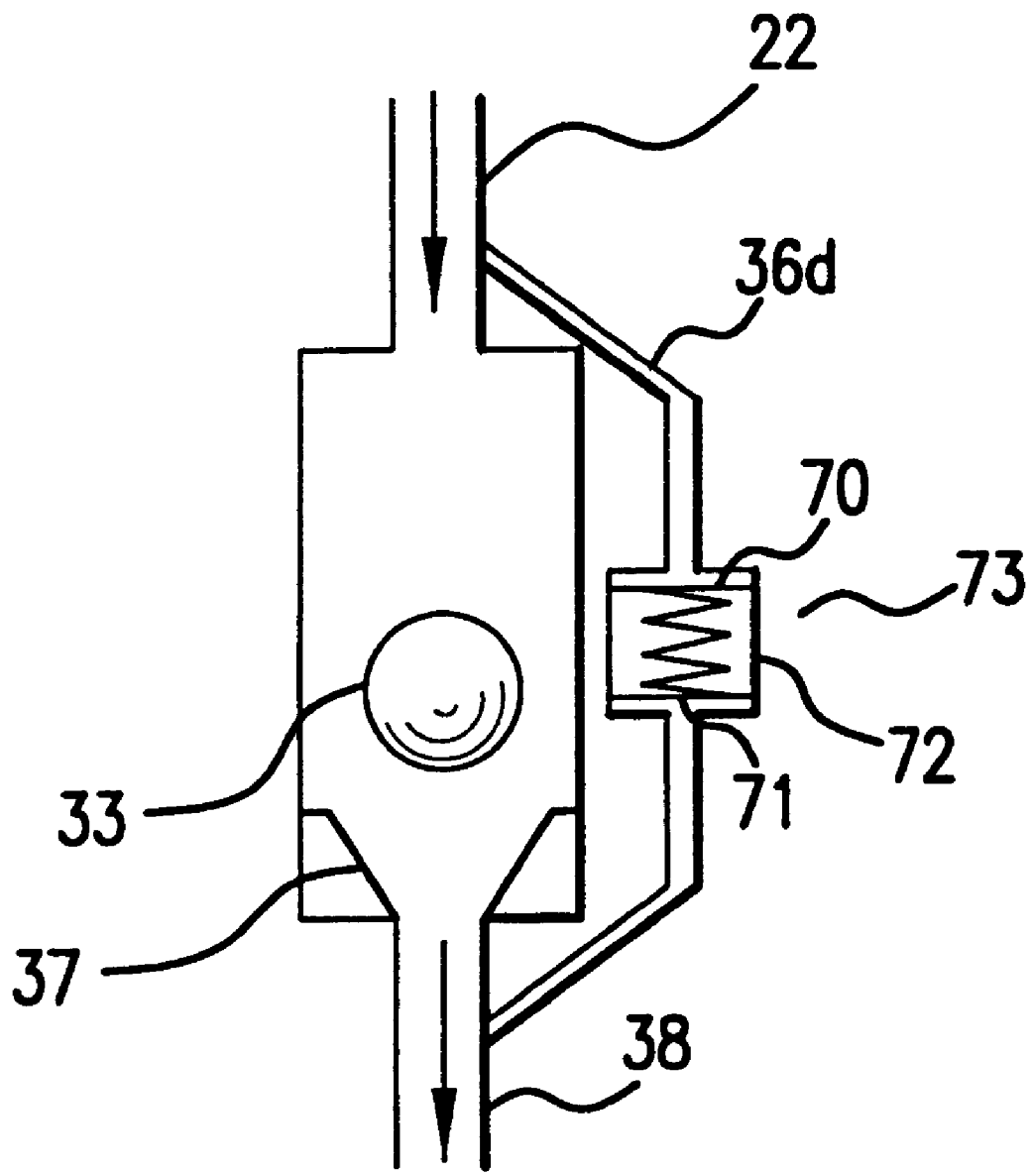
FIG. 7 is an elevation view of another embodiment of a valve for the medical dye delivery system shown in FIG. 1.

In another embodiment shown in FIG. 7, bypass channel 36d includes a bypass valve 70 including a flexible, fenestrated rubber piece 71 disposed in a bypass valve seat 72. Fenestrated rubber piece 71 is of the same diameter as bypass valve seat 72 and acts as a seal, forcing fluid through one or more openings 73 in rubber piece 71 that collectively have a substantially smaller area than the opening through valve seat 37.

Figure 8:
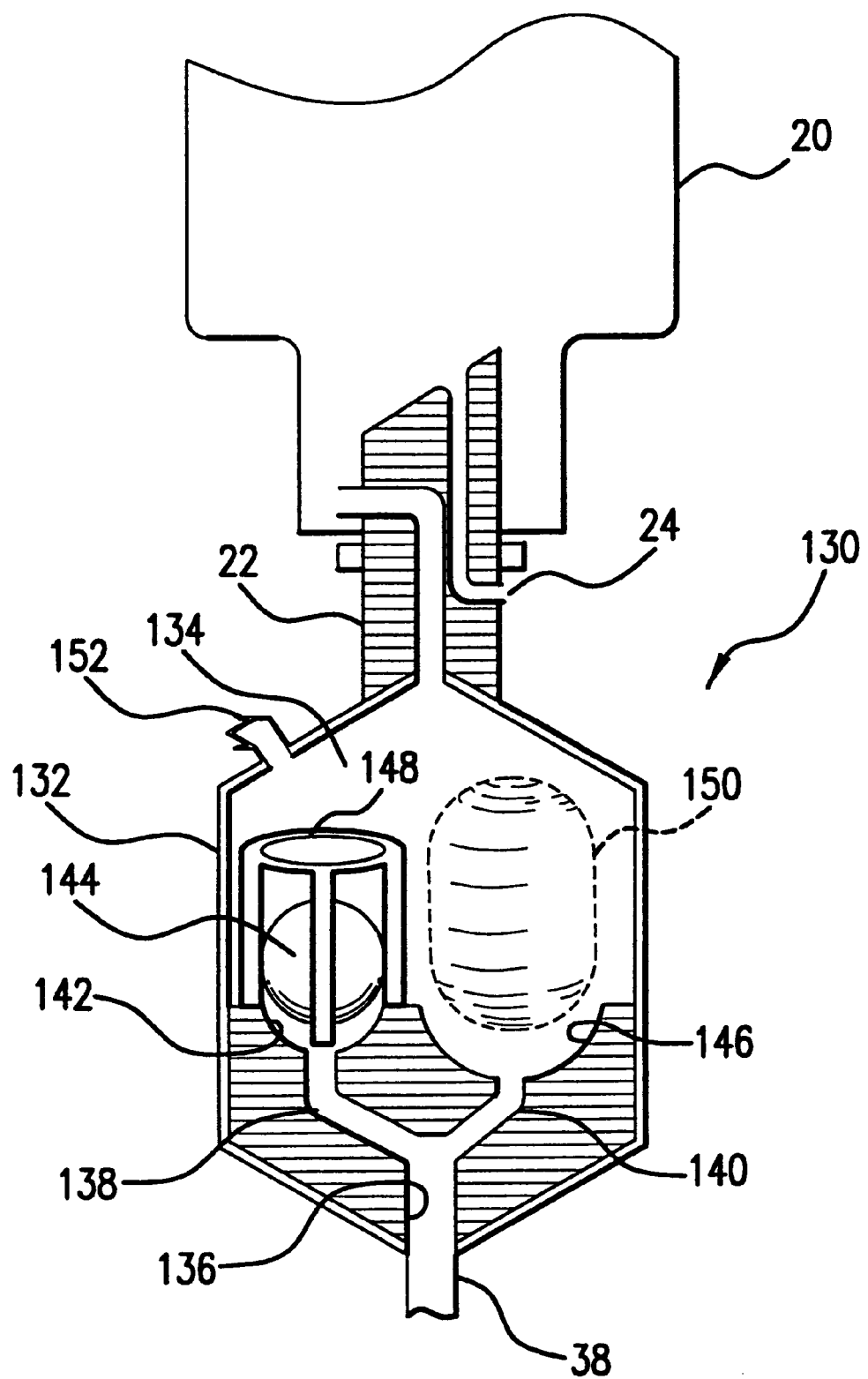
FIG. 8 is an elevation view of another embodiment of a valve for the medical dye delivery system shown in FIG. 1.
Figure 9:
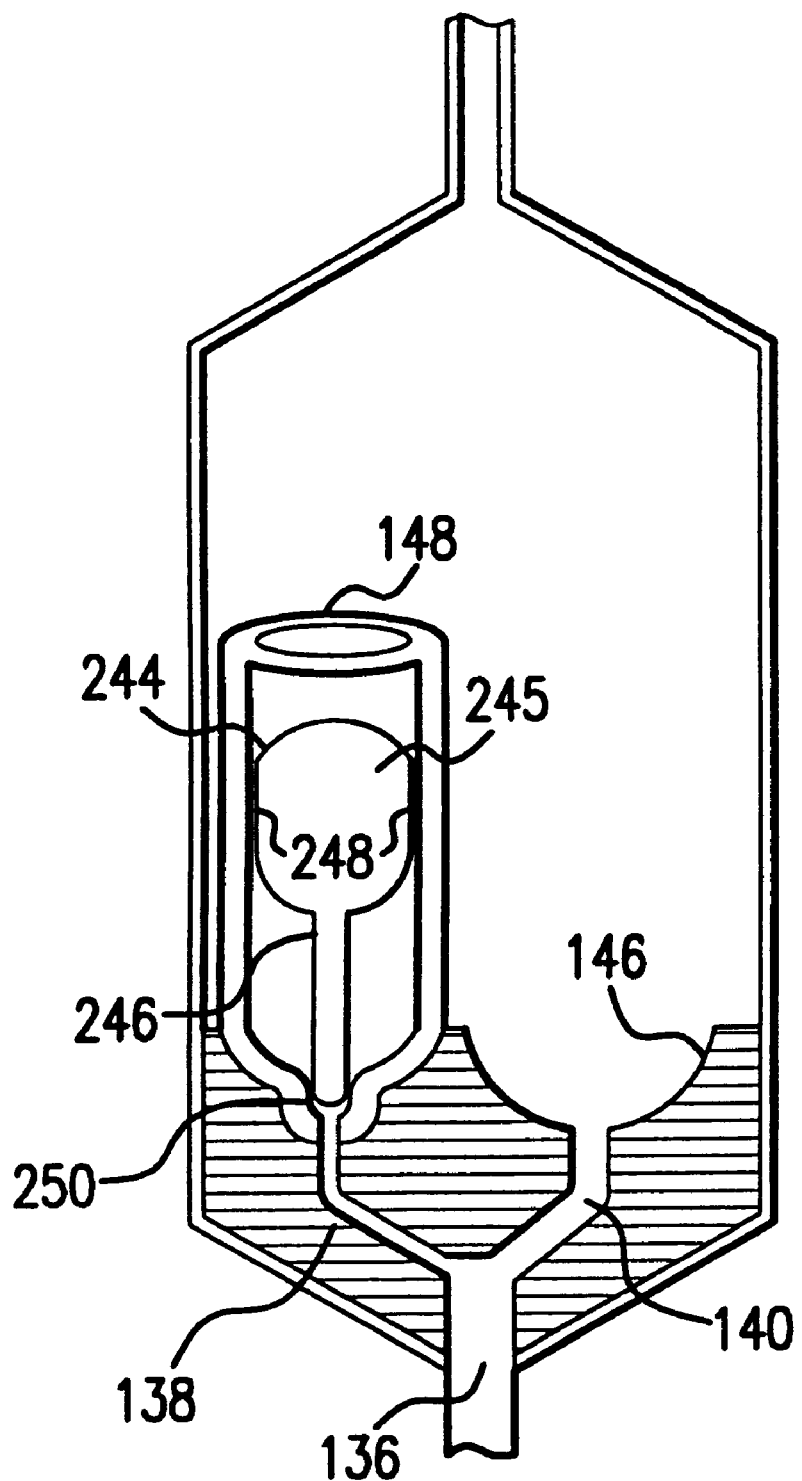
FIG. 9 is an elevation view of another embodiment of a valve for the medical dye delivery system shown in FIG. 1.

Other valve embodiments are shown in FIGS. 8 and 9. As shown in FIG. 8, valve 130 includes a valve housing 132 that defines a flotation chamber 134 for containing medical dye delivered from container 20. A passageway 136 is formed in the bottom of valve housing 132 and is connected in flow communication with conduit 38. Upstream of conduit 38, passageway 136 branches into two separate channels: a dye delivery channel 138 and a bypass channel 140. Like the embodiment shown in FIG. 2, bypass channel 140 has a cross-section that is substantially smaller than delivery channel 138 to provide restricted flow through the system, thereby increasing the force necessary to draw fluid through the system with syringe 10. This gives the operator a tactile warning of the low volume of dye remaining in the system, but still allows the operator to use this remaining dye as so desired. Bypass channel 140 may also include the bypass valve arrangements shown in FIGS. 5–7.

Delivery channel 138 is connected in flow communication with a valve seat 142, which may be conical or hemispherical in shape. As in the previous embodiments, a flotation member or ball 144 is provided in flotation chamber 134 to seat against valve seat 142, when no dye is in flotation chamber 134, and thereby block flow of air or other fluids through delivery channel 138.

Adjacent valve seat 142 is an enlarged opening 146 that leads into bypass channel 140. A small volume of dye will pool in enlarged opening 146 to facilitate flow of dye, instead of air, into bypass channel 140 when delivery channel 138 is blocked by flotation member 144.

To prevent opening 146 from accidentally being blocked by flotation member 144, flotation member 144 is placed within a cage 148 that surrounds valve seat 142. As a result, movement of flotation member 144 within flotation chamber 134 is limited so that flotation member 144 can only rest within valve seat 142 when there is no dye in flotation chamber 134.

To facilitate priming of the system, valve 130 may include an optional elastic priming member 150 that extends outwardly from the exterior of housing 132. Member 150 forms part of the peripheral wall of housing 132, but includes a substantially semi-cylindrical or hemispherical protrusion relative to the remaining, more rigid peripheral wall of housing 132. To prime the system, priming member 150 is depressed and then released to create a suction effect that draws medical dye from container 20 into flotation chamber 134.

Alternatively, selected portions of housing 132 may be made flexible to allow for depression and priming of the system, like priming member 150. The portions of housing 132 that are made flexible are selected so as to not interfere with the function and performance of flotation member 144 and bypass channel 140. For example, the upper portion of housing 132 may be flexible, while the lower portion is rigid.

As another alternative, valve 130 may include a port 152 into which a needle of a syringe is inserted. Actuating the syringe creates suction in chamber 134 to draw medical dye from container 20 into flotation chamber 134. Once priming is achieved, the syringe may be withdrawn from port 152. Port 152 preferably includes a rubber seal that allows for puncture by the syringe and subsequent closure and resealing of the port when the syringe is removed. As another alternative, any of those valves known in the art may be formed in housing 132 to allow air to enter chamber 134 when priming is desired.

Any of the above-described priming methods may be used in each of the disclosed valve embodiments to effect priming.

The embodiment shown in FIG. 9 is identical to that shown in FIG. 8 except for the geometries of the flotation member and the valve seat. As shown in FIG. 9, flotation member 244 includes a substantially cylindrical top portion 245 and an elongated, slender portion 246 extending downwardly from portion 245. In addition, the valve seat is modified to include a small, concave portion 250 that is sized to mate with the similarly-shaped end of member 246 to tightly seal delivery channel 138.

The configuration of the flotation member 244 is based on two design requirements: sufficient buoyancy in the medical dye and effective sealing of the delivery channel. Medical dye typically has a low specific gravity, but a high viscosity. Thus, the flotation member must have sufficient buoyancy to float in the medical dye, but also have sufficient weight to seal against the valve seat. The flotation member 244 shown in FIG. 9 accomplishes these design requirements by minimizing the surface areas of the flotation member and valve seat required to seal the delivery channel. Flotation member 244 also uses the greater weight of the top member 245 to press down on lower member 246 to firmly press it against valve seat 250. The total weight of member 244 may be made lighter than members required to seal a valve seat as shown, for example, in FIG. 8.

To control the orientation of flotation member 244 within cage 148, sides 248 of flotation member 244 are flattened and are spaced at close tolerances relative to the side walls of cage 148. As a result, member 246 will mate with concave portion 250 of the valve seat to tightly seal delivery channel 138.

In the embodiments described above, the valve member 30 has been described as a separate element from the medical dye container 20, separated from the container by a length of conduit 22. However, it is possible to modify the medical valve container 20 to incorporate the valve 30. For example, the valve 30 can be an integral and/or internal part of the container 20, or otherwise incorporated into an outlet of the container 20 to minimize the length of the conduit 22 in the system illustrated in FIG. 1.

Figure 10:
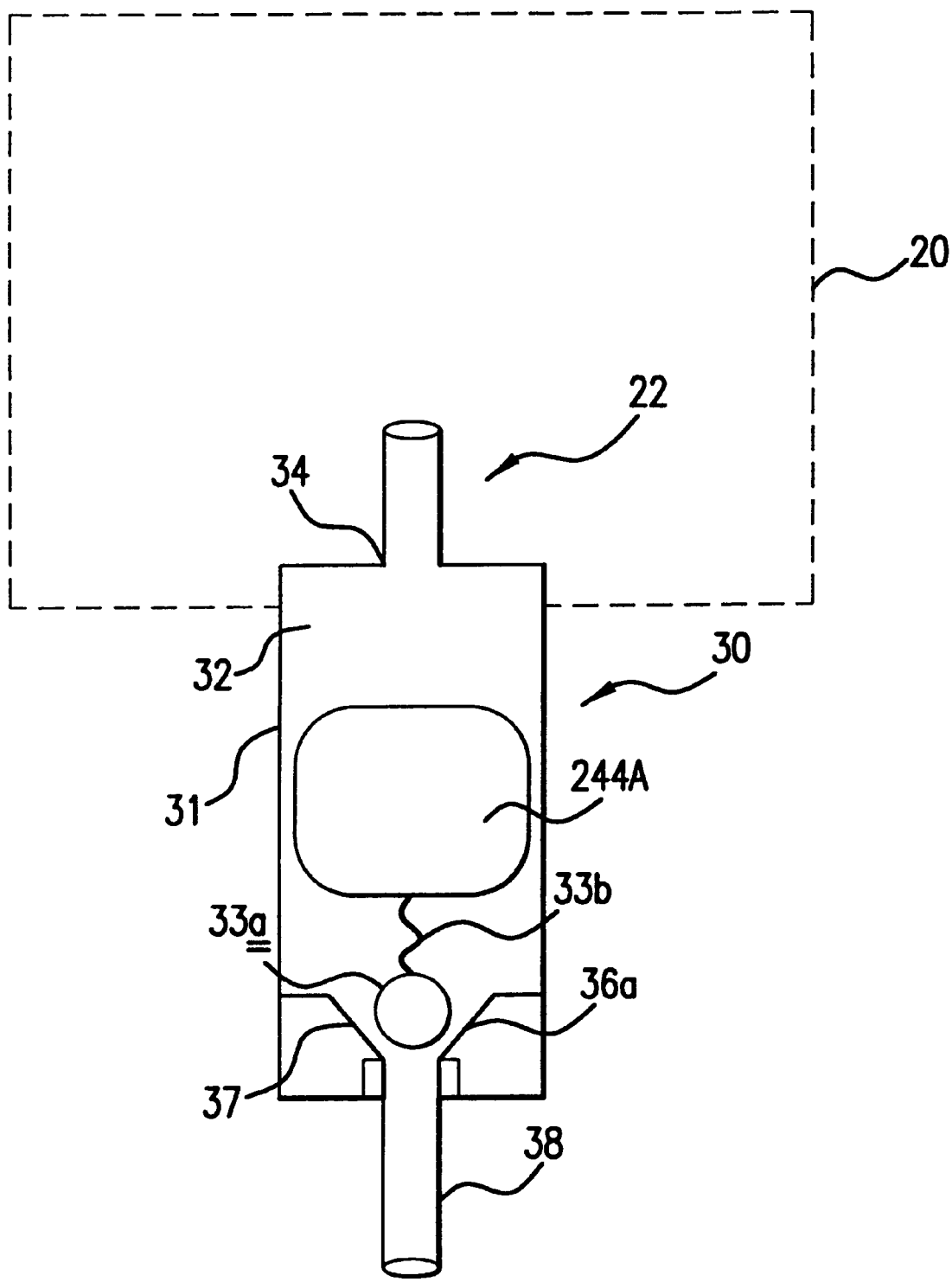
FIG. 10 is an elevation view of another embodiment of a valve for the medical dye delivery system of FIG. 1 where the valve is incorporated into the medical dye container.
Figure 11A:
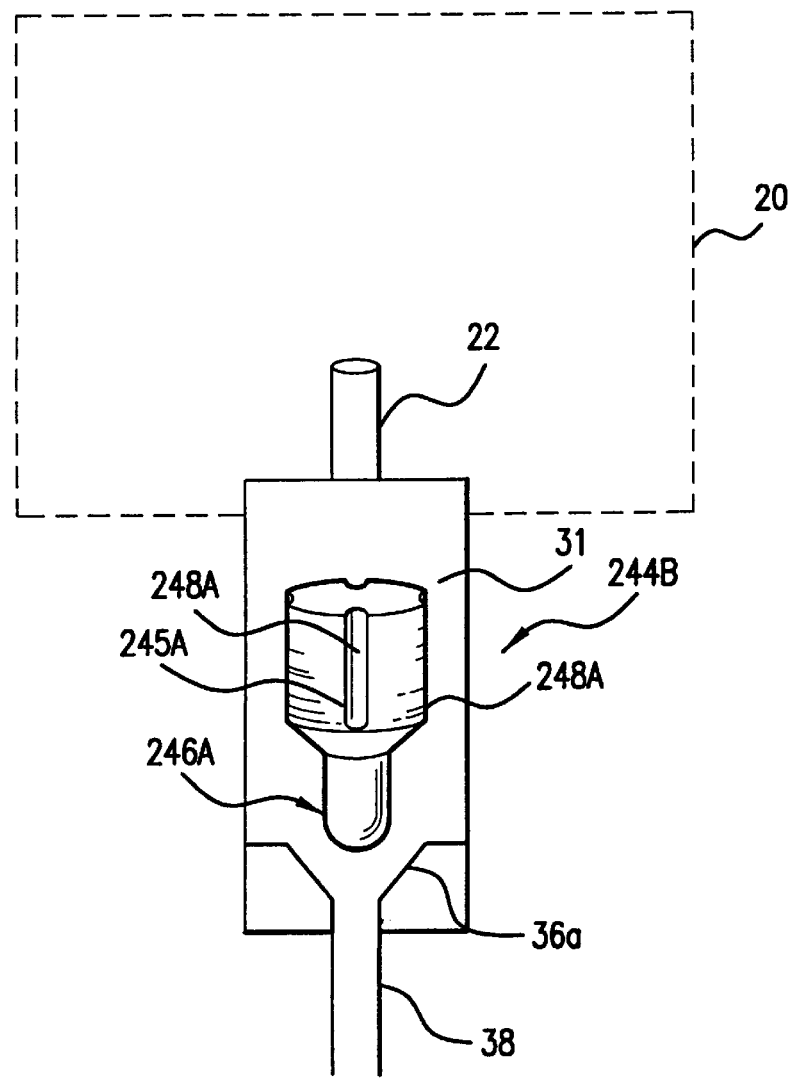
FIG. 11A is an elevational view of another embodiment of a valve for the medical due delivery system of FIG. 1 where the valve is incorporated into the medical dye container.
Figure 11B:
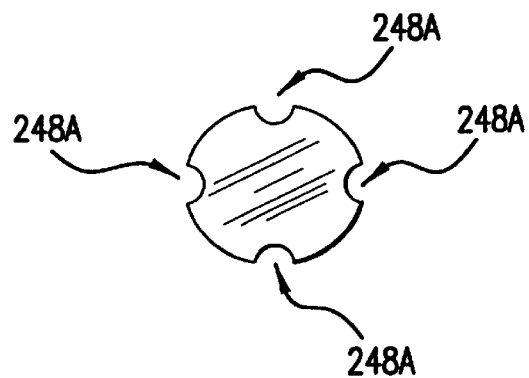
FIG. 11B is a cross-sectional view of the flotation member illustrated in FIG. 11A.

FIGS. 10, 11A and 11B illustrate embodiments that may be readily incorporated into the medical dye container. In FIGS. 10, 11A and 11B, the medical dye container 20 is shown in phantom with the valve 30 and conduit 22 shown in solid lines to represent that the valve 30 could be incorporated into container 20. However, it is also possible that the valve 20 of FIGS. 10 and 11A could be a separate element from the container 20 but in fluid communication by the conduit 22.

In FIG. 10, a ball or weight 33a is suspended by a tether 33b from a flotation device 244A. The weight of the ball 33a is heavy enough to seal against the valve seat 37, but light enough to be suspended from the flotation device 244A when the amount of dye in the container is sufficient to allow flotation device 244A to float on the surface of the dye.

In FIGS. 11A and 11B, the flotation member 244B has a top member 245A and lower member 246A. Like FIGS. 9 and 10, the lower member 246A is heavier than the top member 245A, but light enough to allow the top member 245A to float on the dye surface. The upper member 245A may be hollow and flexible, while the lower member 246A is preferably solid or heavier than the upper member 245A.

In the embodiment of FIG. 11A, like the embodiment of FIG. 10, the valve includes a light member to float on the dye surface and a heavy member suspended from the light member to close against the valve seat. This structure is accomplished in FIG. 10 with two pieces: a flotation member 244A and a ball or weight 33a suspended from the flotation member 244A by the tether 33b. In FIG. 11, the structure is accomplished by one piece: a flotation member 244B with a hollow top portion 245A and a heavy or solid lower portion 246A. In either the one piece structure of FIG. 11A or the two piece structure of FIG. 10, there is a change in the density of the valve member from a relatively low density upper portion that enables the valve member to float on the dye surface to a relatively high density lower portion that closes against the valve seat. The densities of the upper and lower portions are determined by choosing a density for the lower portion that is sufficient to close against the valve seat yet is still capable of being suspended above the valve seat as the upper portion floats on the dye surface.

As illustrated in FIGS. 11A and 11B, the upper member 245A has several channels 248A in the sides 248 for the dye to flow around the upper member 245A from the inlet to the outlet. Therefore, as the flotation member 244 floats on the dye surface while the dye is being depleted, the dye can flow through the channels 248A to the outlet 35 until the lower member 246A seats on the valve seat 37.

Any one of the bypass channel structures described above in FIGS. 2–9 could be incorporated into the valve 30 illustrated in FIGS. 10, 11A and 11B. For example, the bypass channel could be a slot in the valve seat 37, like the slot 36 illustrated in FIG. 4; or the bypass channel could be a separate channel around the valve seat like the channel 36 in FIG. 2.

Each of the above-described valve embodiments may be composed of plastic or any suitable materials designed for medical use.

It will be apparent to those skilled in the art that various modifications and variations can be made in the medical dye delivery system of the present invention without departing from the spirit or scope of the invention. For example, the bypass channel may be eliminated from each of the above-disclosed valve embodiments. Instead, when the operator senses increased resistance when the flotation member seats against the valve seat, the operator may terminate dye delivery and proceed with the angiography procedure or, if the remaining dye in the system is to be used, the operator may manipulate the valve (e.g. by turning the valve sideways to unseat the flotation member from the valve seat) and withdraw the remaining dye into the syringe for delivery to the patient. Thus, it is intended that the present invention cover the modifications and variations of this invention.

What is claimed is:

1. A medical dye delivery system for delivering medical dye through a system flow path to a patient, comprising:
    a medical dye container;
    a device for withdrawing medical dye from the container and directing the medical dye through the system flow path into a patient; and
    a valve having an inlet in flow communication with the medical dye container and an outlet in flow communication with the withdrawing device, the valve including a housing defining a chamber adapted for containing a volume of the medical dye, a valve seat located in the chamber and having an opening therethrough in flow communication with the outlet, and a flotation member in the chamber, the flotation member adapted for floating in the volume of medical dye and being seated against the valve seat when the chamber is substantially free of medical dye to cover the valve seat opening,
    wherein the flotation member comprises a first portion and a second portion extending from the first portion, the second portion having a density greater than a density of the first portion such that the density of the second portion is sufficient to close against the valve seat but is capable of being suspended above the valve seat when the flotation member floats in the volume of medical dye.

2. The medical dye delivery system of claim 1, wherein the valve is incorporated into the medical dye container.

3. The medical dye delivery system of claim 1, wherein the valve is separated from the medical dye container by a conduit extending from the medical dye container.

4. The medical dye delivery system of claim 1, wherein the second portion is suspended from the first portion by a tether.

5. The medical dye delivery system of claim 4, wherein the second portion has a spherical shape for seating against the valve seat.

6. The medical dye delivery system of claim 1, wherein the first and second portions are part of a one-piece flotation member.

7. The medical dye delivery system of claim 1, wherein first portion is hollow.

8. The medical dye delivery system of claim 1, wherein the second portion is solid.

9. The medical dye delivery system of claim 1, wherein the first portion has a peripheral side surface with at least one channel that allows the medical dye to flow from the valve inlet to the valve outlet.

10. A valve for medical dye delivery system comprising:
a housing having an inlet and an outlet and defining a chamber adapted for containing a volume of medical dye, a valve seat located in the chamber and having an opening therethrough in flow communication with the outlet, and a flotation member in the chamber, the flotation member adapted for floating in the volume of medical dye and being seated against the valve seat when the chamber is substantially free of medical dye to cover the valve seat opening, wherein the flotation member comprises a first portion and a second portion extending from the first portion, the second portion having a density greater than a density of the first portion such that the density of the second portion is sufficient to close against the valve seat but is capable of being suspended above the valve seat when the flotation member floats in the volume of medical dye.

11. The valve of claim 10, wherein the valve is incorporated into a medical dye container.

12. The valve of claim 10, wherein the valve is in fluid communication with but separated from a medical dye container by a conduit extending from the medical dye container.

13. The valve of claim 10, wherein the second portion is suspended from the first portion by a tether.

14. The valve of claim 13, wherein the second portion has a spherical shape for seating against the valve seat.

15. The valve of claim 10, wherein the first and second portions are part of a one-piece flotation member.

16. The valve of claim 10, wherein first portion is hollow.

17. The valve of claim 10, wherein the second portion is solid.

18. The valve of claim 10, wherein the first portion has a peripheral side surface with at least one channel that allows the medical dye to flow from the valve inlet to the valve outlet.

\* \* \* \* \*